(12) United States Patent
Zhou et al.

(10) Patent No.: US 11,040,336 B2
(45) Date of Patent: Jun. 22, 2021

(54) CATALYST OF PLATINUM/ZIRCONIUM DIOXIDE/SBA-15 AND METHOD FOR PREPARING P-CHLOROANILINE USING THE SAME

(71) Applicant: Xiangtan University, Xiangtan (CN)

(72) Inventors: Jicheng Zhou, Xiangtan (CN); Yanji Zhang, Xiangtan (CN); Fei Wang, Xiangtan (CN)

(73) Assignee: XIANGTAN UNIVERSITY, Xiangtan (CN)

( * ) Notice: Subject to any disclaimer, the term of this patent is extended or adjusted under 35 U.S.C. 154(b) by 0 days.

(21) Appl. No.: 16/901,029

(22) Filed: Jun. 15, 2020

(65) Prior Publication Data

US 2020/0306735 A1    Oct. 1, 2020

Related U.S. Application Data

(63) Continuation-in-part of application No. PCT/CN2018/120710, filed on Dec. 12, 2018.

(30) Foreign Application Priority Data

Dec. 14, 2017   (CN) .......................... 201711340003.X
Dec. 14, 2017   (CN) .......................... 201711340016.7

(51) Int. Cl.
    *C07C 209/36*    (2006.01)
    *C07C 211/52*    (2006.01)
    *B01J 29/03*     (2006.01)
    *B01J 37/02*     (2006.01)
    (Continued)

(52) U.S. Cl.
    CPC ....... *B01J 29/0325* (2013.01); *B01J 37/0228* (2013.01); *B01J 37/0236* (2013.01); *B01J 37/0244* (2013.01); *B01J 37/088* (2013.01); *B01J 37/343* (2013.01); *B01J 37/345* (2013.01); *C07C 209/365* (2013.01); *C07C 211/52* (2013.01)

(58) Field of Classification Search
    None
    See application file for complete search history.

(56) References Cited

U.S. PATENT DOCUMENTS

2007/0049772 A1    3/2007    Liu et al.
2017/0001180 A1    1/2017    Ravishankar et al.

FOREIGN PATENT DOCUMENTS

| CN | 1886193 A   | 12/2006 |
|----|-------------|---------|
| CN | 101069847 A | 11/2007 |
| CN | 101462050 A | 6/2009  |

(Continued)

OTHER PUBLICATIONS

Wang ("TiO2 and ZrO2 crystals in SBA-15 silica: performance of Pt/TiO2(ZrO2)/SBA-15 catalysts in ethyl acetate combustion" Journal of Catalysis, 222, 2004, p. 565-571) (Year: 2004).*

(Continued)

*Primary Examiner* — Amy C Bonaparte
(74) *Attorney, Agent, or Firm* — Matthias Scholl P.C.; Matthias Scholl

(57) ABSTRACT

A catalyst including platinum (Pt) and a composite support. The composite support includes $ZrO_2$/mesoporous silica sieve SBA-15. The platinum accounts for 0.01-0.3 wt. % of the catalyst. $ZrO_2$ accounts for 5-20 wt. % of the composite support.

9 Claims, 2 Drawing Sheets

(51) Int. Cl.
  *B01J 37/08*  (2006.01)
  *B01J 37/34*  (2006.01)

(56) References Cited

FOREIGN PATENT DOCUMENTS

| CN | 101745382 A | 6/2010 |
|---|---|---|
| CN | 102633581 A | 8/2012 |
| CN | 103007978 A | 4/2013 |
| CN | 104039442 A | 9/2014 |
| CN | 105195238 A | 12/2015 |
| CN | 105562032  * | 5/2016 |
| CN | 105562032 A | 5/2016 |

OTHER PUBLICATIONS

Jiang ("CVD or Pt(C5H9)2 to Synthesize Highly Dispersed Pt/SBA-15 Catalysts for Hydrogenation of Chloronitrobenzene", Chem. Vap. Deposition, 2014, 20, p. 146-151) (Year: 2014).*

Wenli Zheng, Pt Nanoparticles Supported on Highly-dispersed Titania Coated Inside Mesoporous Materials for Efficient Catalytic Hydrogenation, Master's thesis, Jan. 2013, pp. 25-27 & B021-71, vol. 01, China Master's Theses Full-text Database, China.

Xiaohong Li et al., Pt nanoparticles supported on highly dispersed TiO2 coated on SBA-15 as an efficient and recyclable catalyst for liquid-phase hydrogenation, Journal of Catalysis, Apr. 2013, pp. 9-19, vol. 300, Elsevier, Shanghai, China.

Xiangdong Jiao et al., Catalytic performance of Pt—Au/TiO2 for p-chloronitrobenzene hydrogenation, Applied Chemical Industry, Oct. 2010, pp. 1485-1487 & 1501, V01. 39 No. 10, Shaanxi Research Design Institute of Petroleum and Chemical Industry, Xi'an, China.

* cited by examiner

CATALYST OF PLATINUM/ZIRCONIUM DIOXIDE/SBA-15 AND METHOD FOR PREPARING P-CHLOROANILINE USING THE SAME

CROSS-REFERENCE TO RELATED APPLICATIONS

This application is a continuation-in-part of International Patent Application No. PCT/CN2018/120710 with an international filing date of Dec. 12, 2018, designating the United States, now pending, and further claims foreign priority benefits to Chinese Patent Application No. 201711340003.X filed Dec. 14, 2017, and to Chinese Patent Application No. 201711340016.7 filed Dec. 14, 2017. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND

The disclosure relates to a catalyst of platinum/$ZrO_2$/SBA-15 and a method for preparing p-chloroaniline using the catalyst.

p-Chloroaniline (4-chloroaniline) is an organochlorine compound used in the industrial production of pesticides, drugs, and dyestuffs. p-Chloroaniline is prepared by reduction of p-chloronitrobenzene through metal, non-hydrogen reducing agent, or catalytic hydrogenation. Particularly, the catalytic hydrogenation reduction is widely used. However, the catalytic hydrogenation reduction involves a dechlorination reaction, thus adversely affecting the selectivity for the target product.

SUMMARY

The disclosure provides a catalyst for selective hydrogenation of chlorinated aromatic nitro compounds. The catalyst comprises platinum (Pt) and a composite support. The composite support comprises $ZrO_2$/mesoporous silica sieve SBA-15. The platinum accounts for 0.01-0.3 wt. % of the catalyst, particularly, 0.05-0.15 wt. %, and more particularly, 0.08-0.10 wt. %.

$ZrO_2$ accounts for 5-20 wt. % of the composite support, particularly, 10-15 wt. %.

In certain embodiments of the disclosure, platinum interacts with semiconductor metal oxide $ZrO_2$ to form composite nanostructured catalyst Pt/$ZrO_2$/SBA-15; specifically, the interaction of nanometal platinum and nano zirconia can maintain the catalytic activity of the catalyst with a small amount of platinum, thus reducing the cost of the catalyst.

In certain embodiments of the disclosure, the $ZrO_2$ is a film structure coating the mesoporous silica sieve SBA-15, and the platinum is disposed on the film structure of $ZrO_2$. The $ZrO_2$ is a single layer or multi-layer coating on the SBA-15.

The disclosure also provides a method for preparing the catalyst, the method comprising: precipitating $ZrO_2$ on the mesoporous silica sieve SBA-15, thereby yielding a composite support comprising $ZrO_2$/SBA-15; and disposing platinum on the composite support through a photocatalytic reduction method, thereby yielding Pt/$ZrO_2$/SBA-15.

In certain embodiments of the disclosure, precipitating $ZrO_2$ on the mesoporous silica sieve SBA-15 comprises: adding SBA-15 to a zirconium oxychloride solution, adjusting the pH of the zirconium oxychloride solution mixed with the SBA-15 to 4-6, stirring the zirconium oxychloride solution mixed with the SBA-15 at normal temperature for 0.5 hours, sonicating the zirconium oxychloride solution mixed with the SBA-15 for 0.5 hours, resting the zirconium oxychloride solution mixed with the SBA-15 for one night, drying the zirconium oxychloride solution mixed with the SBA-15 at 110° C. for one night, and calcinating at 500° C., thereby yielding a composite support comprising $ZrO_2$/SBA-15.

The photocatalytic reduction method comprises: dispersing the composite support in deionized water, adding a mixture of methanol and chloroplatinic acid to the deionized water comprising the composite support, sonicating a solution of the mixture and the deionized water comprising the composite support, exposing and stirring the solution sonicated under UV irradiation, filtering the solution thereby producing a solid, collecting and washing the solid to have a pH of 7, and drying the solid, thereby yielding the Pt/$ZrO_2$/SBA-15.

The mass ratio of the methanol to the deionized water is 1:5-1:15, and the solution is exposed under UV irradiation for 5-20 hours.

The disclosure further provides a method for preparing p-chloroaniline, the method comprising mixing the catalyst and p-chloronitrobenzene in the presence of hydrogen.

Specifically, the method for preparing p-chloroaniline comprises: dissolving the catalyst and p-chloronitrobenzene in absolute ethyl alcohol in a reactor, heating the reactor to a temperature of 40-90° C., and purging the reactor with hydrogen.

DETAILED DESCRIPTION

Figure 1:
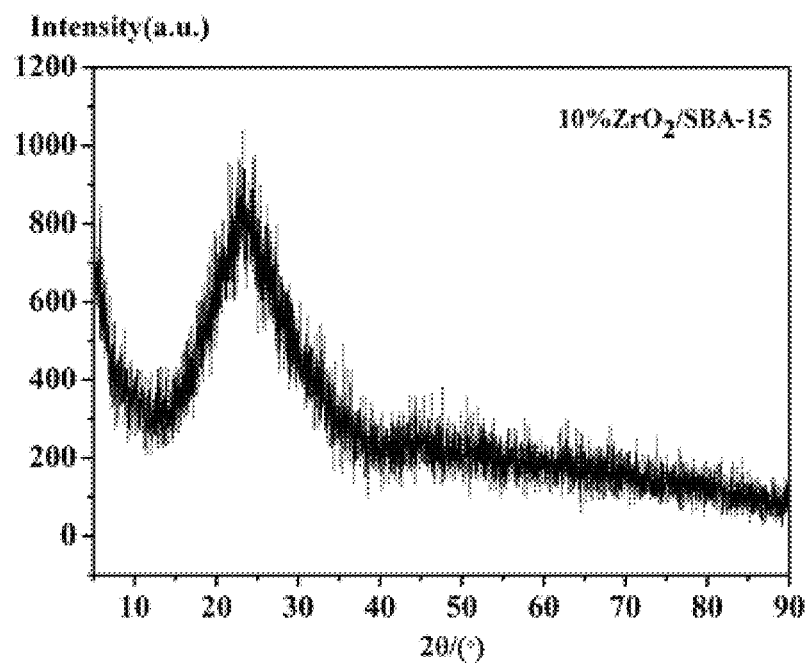
FIG. 1 is an X-ray diffraction graph of a composite support 10 wt. % $ZrO_2$/SBA-15 in accordance with one embodiment of the disclosure.

To further illustrate the disclosure, embodiments detailing a catalyst of platinum/$ZrO_2$/SBA-15 and a method for preparing p-chloroaniline using the catalyst are described below. It should be noted that the following embodiments are intended to describe and not to limit the disclosure.

The disclosure provides a method for preparing p-chloroaniline using the catalyst platinum/$ZrO_2$/SBA-15, the method comprising:

1) dissolving platinum/$ZrO_2$/SBA-15 and p-chloronitrobenzene in a solvent in a 50-mL reactor; purging the reactor with hydrogen to remove the air; and setting the temperature and pressure of the reactor;

2) when the reactor reaches the preset temperature, purging the reactor with hydrogen again to perform hydrogenation reaction;

3) cooling the reactor, centrifuging the solution obtained from the reactor, collecting a solid product, analyzing the solid product using gas chromatography; and 4) take an appropriate amount of the reaction liquid into a 10 mL sample bottle, add the internal standard chlorobenzene in it, dilute with an appropriate amount of ethanol, then the prepared solution is ultrasonic dispersed for 10 min, analyzed using an Agilent 6890N GC with an HP-5 capillary column and FID detector. The calculation formula of the content of the component to be measured is as follows:

$$m_i = f_i \times m_{IS} \times \frac{A_i}{A_{IS}} \quad (1\text{-}1)$$

i represents p-chloronitrobenzene (p-CNB), p-chloroaniline (p-CNA) or aniline (NA);

$m_i$ represent the mass of product p-CNB, p-CNA or NA contained in the prepared solution;

$m_{1S}$ represent the mass of the internal standard chlorobenzene added to the prepared solution;

$A_i$ represent the peak area of p-CNB, p-CNA or NA;

$A_{1S}$ indicate the peak area of the internal standard chlorobenzene;

$f_i$ represent the relative correction factor of p-CNB, p-CNA or NA.

Calculate the mass percentage (w) of p-CNA or NA in the prepared solution:

$$w_{p\text{-}CNA} = m_{p\text{-}CNA} / m_{p\text{-}CNB} \times 100\%;$$

$$w_{NA} = m_{NA} / m_{p\text{-}CNB} \times 100\% \quad (1\text{-}2)$$

Calculate the total content ($M_{total}$) of p-CNA and NA in the prepared solution:

$$M_{total,p\text{-}CNA} = w_{p\text{-}CNA} \times m_{p\text{-}CAN};$$

$$M_{total,NA} = w_{NA} \times m_{NA} \quad (1\text{-}3)$$

The conversion (Conv.) of p-CNB and product selectivity (Sel.) are calculated according to the following formula:

Conv.=(Moles of reactants converted)/(Moles of initial reactants)×100%=$(n_{p\text{-}CNA}+n_{NA})/n_{p\text{-}CNB}$×100%=$(M_{total,p\text{-}CNA}/127.57+M_{total,NA}/93.14)/(M_{p\text{-}CNB}/157.56)$×100%;

Sel.=$n_{p\text{-}CNA}/(n_{p\text{-}CNA}+n_{NA})$×100%=$(M_{total,p\text{-}CNA}/127.57)/(M_{total,p\text{-}CNA}/127.57+M_{total,NA}/93.14)$×100%  (1-4).

$n_{p\text{-}CNB}$, $n_{p\text{-}CNA}$, $n_{NA}$ represent molar weights of p-chloronitrobenzene (p-CNB), p-chloroaniline (p-CNA) and aniline (NA), respectively.

Example 1

The mesoporous silica sieve SBA-15 was mixed with 15 mL of absolute ethyl alcohol and the mixture was oscillated under ultrasonic sound. 0.302 g of $ZrOCl_2 \cdot 8H_2O$ was added to 30 mL of deionized water, and the solution was stirred and heated to 85° C. 1 g of the preprocessed mesoporous silica sieve SBA-15 was added to the solution, stirred, and the pH of the mixed solution was adjusted to 4-6 using diluted aqueous ammonia. The mixed solution was stirred under normal temperature for 0.5 hours, sonicated for 0.5 hours, and stayed for one night. Thereafter, the mixed solution was filtered by a vacuum pump and a solid was collected. The solid was washed using deionized water, dried at 110° C. for one night, and calcined in a muffle furnace at 500° C. to yield a composite support 10 wt. ° $ZrO_2$/SBA-15. 0.702 g of 10 wt. % $ZrO_2$/SBA-15 was dispersed in 100 mL of deionized water and 10 mL of absolute methanol was added. The mixture was dispersed under ultrasonic sound for 10 min, followed by addition of 0.1 mL of chloroplatinic acid solution, and further dispersed under ultrasonic sound for 20 min. Thereafter, the dispersed mixture was stirred, exposed under UV irradiation for 12 hours, and filtered. A solid product was collected, washed and vacuum dried at 80° C. to yield Pt/$ZrO_2$/SBA-15 comprising 0.1 wt. % of Pt, that is, 0.1 wt. % wt. Pt/10 wt. °/$ZrO_2$/SBA-15.

Example 2

Pt/$ZrO_2$/SBA-15 was prepared according to the operations in Example 1 expect that the mass percent of Pt was 0.08%, that is, the product was 0.08 wt. % Pt/10 wt. % $ZrO_2$/SBA-15.

Example 3

Pt/$ZrO_2$/SBA-15 was prepared according to the operations in Example 1 expect that the mass percent of $ZrO_2$ in the composite support was 0.08%, that is, the product was 0.1 wt. % Pt/15 wt. % $ZrO_2$/SBA-15.

Example 4

0.1 wt. % Pt/10 wt. % $ZrO_2$/SBA-15 prepared in Example 1 was used for hydrogenation of p-chloronitrobenzene. Specifically, 0.401 g of p-chloronitrobenzene, 0.1 g of 0.1 wt. % Pt/10 wt. % $ZrO_2$/SBA-15, and 20 mL of absolute ethyl alcohol were added to a high-pressure reactor. The reactor was filled with hydrogen to remove the air. The hydrogen valve was shut off. When the reactor reached 70° C., hydrogen was introduced to the reactor again to reach a pressure of 0.7 megapascal. The mixture solution in the reactor was stirred for one hour. Thereafter, the reactor was cooled, and 10 mL of the solution in the reactor was centrifuged. The resulting product was analyzed using gas chromatography. The results showed that the conversion of p-chloronitrobenzene was 100%, and the selectivity for p-chloroaniline was 98.44%.

Example 5

0.1 g of 0.1 wt. % Pt/10 wt. % $ZrO_2$/SBA-15 prepared in Example 1, 0.401 g of p-chloronitrobenzene, and 20 mL of absolute ethyl alcohol were added to a high-pressure reactor. Hydrogen was introduced to the reactor again to reach a pressure of 0.7 megapascal and the mixture in the reactor was allowed to react at 30° C. for 40 min. The operations were basically the same as that in Example 4. The results showed that the conversion of p-chloronitrobenzene was 98.98%, and the selectivity for p-chloroaniline was 99.99%.

Example 6

0.1 g of 0.1 wt. % Pt/10 wt. % $ZrO_2$/SBA-15 prepared in Example 1, 0.401 g of p-chloronitrobenzene, and 20 mL of absolute ethyl alcohol were added to a high-pressure reactor. Hydrogen was introduced to the reactor again to reach a pressure of 0.7 megapascal and the mixture in the reactor was allowed to react at 40° C. for 40 min. The operations were basically the same as that in Example 4. The results showed that the conversion of p-chloronitrobenzene was 99.47%, and the selectivity for p-chloroaniline was 99.99%.

Example 7

0.1 g of 0.1 wt. % Pt/10 wt. % ZrO$_2$/SBA-15 prepared in Example 1, 0.401 g of p-chloronitrobenzene, and 20 mL of absolute ethyl alcohol were added to a high-pressure reactor. Hydrogen was introduced to the reactor again to reach a pressure of 0.7 megapascal and the mixture in the reactor was allowed to react at 40° C. for 40 min. The operations were basically the same as that in Example 4. The results showed that the conversion of p-chloronitrobenzene was 99.26%, and the selectivity for p-chloroaniline was 98.19%.

Example 8

0.1 g of 0.1 wt. % Pt/10 wt. % ZrO$_2$/SBA-15 prepared in Example 1, 0.401 g of p-chloronitrobenzene, and 20 mL of absolute ethyl alcohol were added to a high-pressure reactor. Hydrogen was introduced to the reactor again to reach a pressure of 0.7 megapascal and the mixture in the reactor was allowed to react at 40° C. for 60 min. The operations were basically the same as that in Example 4. The results showed that the conversion of p-chloronitrobenzene was 99.22%, and the selectivity for p-chloroaniline was 99.99%.

Example 9

The solution in the reactor in Example 4 was centrifuged and the supernatant removed. The collected product was centrifuged and washed repeatedly with absolute ethyl alcohol, and then was dried in a vacuum drier at 40° C. for one night. The dried product was a recycled catalyst and was used again for hydrogenation of p-chloronitrobenzene according to the operations in Example 4. The results showed that the conversion of p-chloronitrobenzene was 99.74%, and the selectivity for p-chloroaniline was 99.99%, which showed that the recycled catalyst still exhibited catalytic activity.

Based on the results in Examples 1-9, the catalysts, with different mass fractions of platinum, exhibited catalytic activity for hydrogenation of p-chloronitrobenzene. The platinum content was relatively low and the conversion of catalytic hydrogenation was efficient, and the side reaction of dechlorination was reduced.

Comparison Example 1

The preparation of the catalyst was basically the same as that m Example 1 except that no zirconium dioxide (ZrO$_2$) was added. The prepared catalyst was 0.1 wt. % Pt/SBA-15 (the platinum content was in the catalyst was 0.1 wt. %).

The catalyst was used for hydrogenation of p-chloronitrobenzene according to the operations in Example 4. 0.1 g of 0.1 wt. % Pt/SBA-15, 0.401 g of p-chloronitrobenzene, and 20 mL of absolute ethyl alcohol were added to a high-pressure reactor. Hydrogen was introduced to the reactor again to reach a pressure of 0.7 megapascal and the mixture in the reactor was allowed to react at 70° C. for 2 hours. The results showed that the conversion of p-chloronitrobenzene was 13.05%, and the selectivity for p-chloroaniline was 100%.

Comparison Example 2

The preparation of the catalyst was basically the same as that in Example 1 except that no zirconium dioxide (ZrO$_2$) was added. The prepared catalyst was 0.1 wt. % Pt/SBA-15 (the platinum content was in the catalyst was 0.1 wt. %).

The catalyst was used for hydrogenation of p-chloronitrobenzene according to the operations in Example 4. 0.1 g of 0.1 wt. % Pt/SBA-15, 0.401 g of p-chloronitrobenzene, and 20 mL of absolute ethyl alcohol were added to a high-pressure reactor. Hydrogen was introduced to the reactor again to reach a pressure of 0.7 megapascal and the mixture in the reactor was allowed to react at 70° C. for 3 hours. The results showed that the conversion of p-chloronitrobenzene was 53.7%, and the selectivity for p-chloroaniline was 100%.

Comparison Example 3

The preparation of the catalyst was basically the same as that in Example 1 except that no zirconium dioxide (ZrO$_2$) was added. The prepared catalyst was 2% Pt/SBA-15 (the platinum content was in the catalyst was 2 wt. %).

The catalyst was used for hydrogenation of p-chloronitrobenzene according to the operations in Example 4. 0.1 g of 2% Pt/SBA-15, 0.401 g of p-chloronitrobenzene, and 20 mL of absolute ethyl alcohol were added to a high-pressure reactor. Hydrogen was introduced to the reactor again to reach a pressure of 0.7 megapascal and the mixture in the reactor was allowed to react at 70° C. for one hour. The results showed that the conversion of p-chloronitrobenzene was 91.51%, and the selectivity for p-chloroaniline was 86.56%.

According to Comparison Examples 1 and 3, when no zirconium dioxide was dispersed on the SBA-15, and the platinum was directly precipitated on the SBA-15, the catalyst having higher content of platinum had better catalytic activity. The conversion rate of the raw material increased, while the side reaction of dechlorination was also increased. Only by dispersing zirconium dioxide on the SBA-15 and platinum on zirconia can the catalysts with excellent catalytic activity and selectivity for target products be prepared at a relatively low platinum content.

According to the results in Comparison Examples 1-3 and Examples 4-9, when zirconia and platinum were successively dispersed on the support SBA-15 to prepare the catalyst of the disclosure for the selective hydrogenation of p-chloronitrobenzene to prepare p-chloroaniline, the catalyst comprising only a small amount of platinum also exhibited catalytic activity, and the side reaction of dechlorination was reduced.

Figure 2:
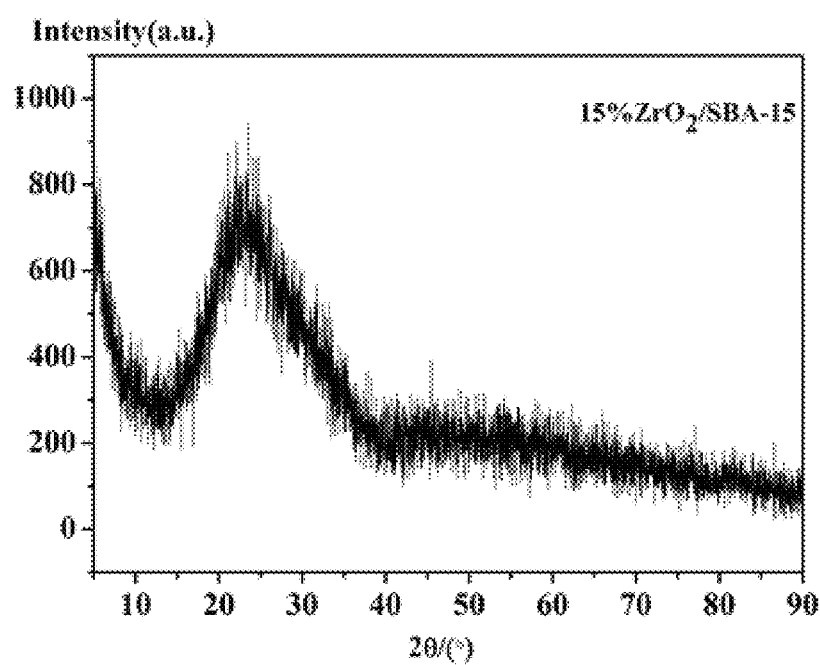
FIG. 2 is an X-ray diffraction graph of a composite support 15 wt. % $ZrO_2$/SBA-15 in accordance with one embodiment of the disclosure.
Figure 3:
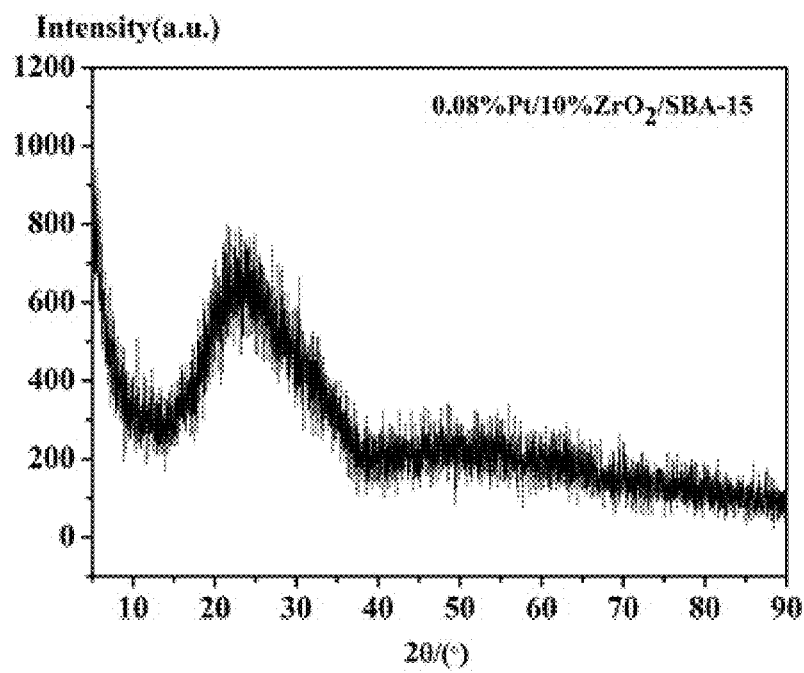
FIG. 3 is an X-ray diffraction graph of a catalyst 0.08 wt. % Pt/10 wt. % $ZrO_2$/SBA-15 in accordance with one embodiment of the disclosure.
Figure 4:
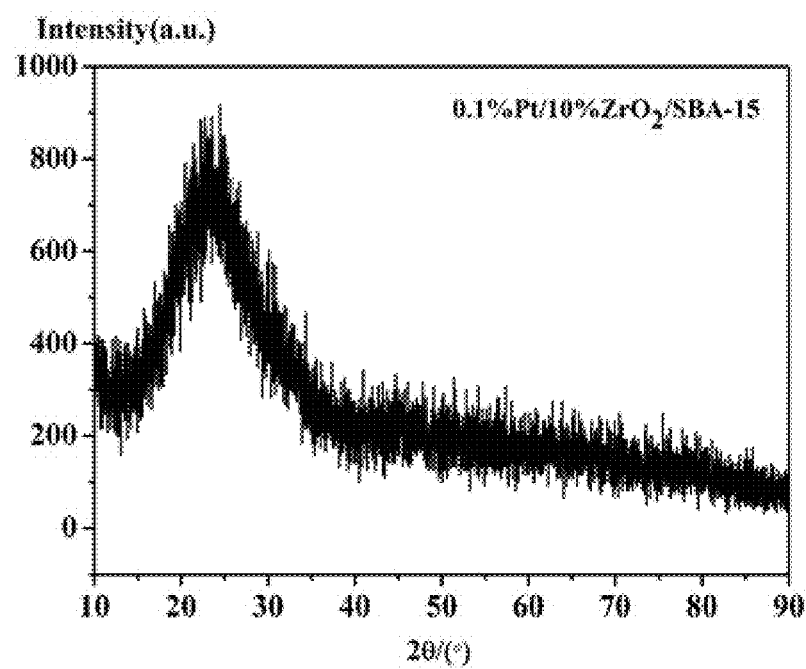
FIG. 4 is an X-ray diffraction graph of a catalyst 0.1 wt. % Pt/10 wt. % $ZrO_2$/SBA-15 in accordance with another embodiment of the disclosure.

FIG. 1 and FIG. 2 are X-ray diffraction graphs of the composite support ZrO$_2$/SBA-15. FIG. 3 and FIG. 4 are X-ray diffraction graphs of the catalyst Pt/ZrO$_2$/SBA-15. By comparing FIGS. 3-4 and FIGS. 1-2, the diffraction peak of platinum can hardly be observed in the XRD graphs, which shows that the platinum content in the catalyst of the disclosure is very low.

Comparison Example 4

The preparation of the catalyst was basically the same as that in Example 1 except that no support SBA-15 was added. The prepared catalyst was 0.1 wt. % Pt/ZrO$_2$ (the platinum content was in the catalyst was 0.1 wt. %).

The catalyst was used for hydrogenation of p-chloronitrobenzene according to the operations in Example 4. 0.1 g of 0.1 wt. % Pt/ZrO$_2$, 0.401 g of p-chloronitrobenzene, and 20 mL of absolute ethyl alcohol were added to a high-pressure reactor. Hydrogen was introduced to the reactor again to reach a pressure of 0.7 megapascal and the mixture in the reactor was allowed to react at 40° C. for 40 min. The results showed that the conversion of p-chloronitrobenzene was 11.70%, and the selectivity for p-chloroaniline was 99.99%.

Compared with Example 4, the catalyst in this example had no support SBA-15, and platinum was directly carried by $ZrO_2$. The conversion of p-chloronitrobenzene decreased.

Example 10

0.1 wt. % Pt/10 wt. % $ZrO_2$/SBA-15 prepared in Example 1 was used for hydrogenation reaction of o-chloronitrobenzene. Specifically, 0.401 g of o-chloronitrobenzene, 0.1 g of 0.1 wt. % Pt/10 wt. % $ZrO_2$/SBA-15, and 20 mL of absolute ethyl alcohol were added to a high-pressure reactor. The reactor was filled with hydrogen to remove the air. The hydrogen valve was shut off. When the reactor reached 80° C., hydrogen was introduced to the reactor again to reach a pressure of 0.7 megapascal. The mixture solution in the reactor was stirred for 60 min. Thereafter, the reactor was cooled, and 10 mL of the solution in the reactor was centrifuged. The resulting product was analyzed using gas chromatography. The results showed that the conversion of o-chloronitrobenzene was 100%, and the selectivity for o-chloroaniline was 97.5%.

Example 11

0.1 g of 0.1 wt. % Pt/10 wt. %/$ZrO_2$/SBA-15 prepared in Example 1, 0.401 g of m-chloronitrobenzene, and 20 mL of absolute ethyl alcohol were added to a high-pressure reactor. Hydrogen was introduced to the reactor again to reach a pressure of 0.7 megapascal and the mixture in the reactor was allowed to react at 40° C. for 40 min. The operations were basically the same as that in Example 10. The results showed that the conversion of m-chloronitrobenzene was 100%, and the selectivity for m-chloroaniline was 99.99%.

Example 12

0.1 g of 0.1 wt. % Pt/10 wt. % $ZrO_2$/SBA-15 prepared in Example 1, 0.401 g of nitrobenzene, and 20 mL of absolute ethyl alcohol were added to a high-pressure reactor. Hydrogen was introduced to the reactor again to reach a pressure of 0.7 megapascal and the mixture in the reactor was allowed to react at 40° C. for 50 min. The operations were basically the same as that in Example 10. The results showed that the conversion of nitrobenzene was 100%, and the selectivity for aniline was 99.99%.

Example 13

0.05 g of 0.1 wt. % Pt/10 wt. % $ZrO_2$/SBA-15 prepared in Example 1, 0.181 g of o-methyl nitrobenzene, and 20 mL of absolute ethyl alcohol were added to a high-pressure reactor. 1 megapascal hydrogen was introduced to the reactor and the mixture in the reactor was allowed to react at 80° C. for 30 min. The operations were basically the same as that in Example 10. The results showed that the conversion of o-methyl nitrobenzene was 100%, and the selectivity for o-methylnitroaniline was 99.99%.

Example 14

0.05 g of 0.1 wt. % Pt/10 wt. % $ZrO_2$/SBA-15 prepared in Example 1, 0.181 g of m-methyl nitrobenzene, and 20 mL of absolute ethyl alcohol were added to a high-pressure reactor. 1 megapascal hydrogen was introduced to the reactor and the mixture in the reactor was allowed to react at 80° C. for 30 min. The operations were basically the same as that in Example 10. The results showed that the conversion of m-methyl nitrobenzene was 100%, and the selectivity for m-methylnitroaniline was 99.99%.

Example 15

0.05 g of 0.1 wt. % Pt/10 wt. % $ZrO_2$/SBA-15 prepared in Example 1, 0.181 g of p-methyl nitrobenzene, and 20 mL of absolute ethyl alcohol were added to a high-pressure reactor. 1 megapascal hydrogen was introduced to the reactor and the mixture in the reactor was allowed to react at 80° C. for 30 min. The operations were basically the same as that in Example 10. The results showed that the conversion of p-methyl nitrobenzene was 100%, and the selectivity for p-methylnitroaniline was 99.99%.

Example 16

0.05 g of 0.1 wt. % Pt/10 wt. % $ZrO_2$/SBA-15 prepared in Example 1, 0.301 g of p-bromonitrobenzene, and 20 mL of absolute ethyl alcohol were added to a high-pressure reactor. Hydrogen was introduced to the reactor again to reach a pressure of 0.7 megapascal and the mixture in the reactor was allowed to react at 60° C. for 30 min. The operations were basically the same as that in Example 10. The results showed that the conversion of p-bromonitrobenzene was 100%, and the selectivity for p-bromoaniline was 99.99%.

Example 17

0.05 g of 0.1 wt. % Pt/10 wt. % $ZrO_2$/SBA-15 prepared in Example 1, 0.211 g of p-fluoronitrobenzene, and 20 mL of absolute ethyl alcohol were added to a high-pressure reactor. 1 megapascal hydrogen was introduced to the reactor and the mixture in the reactor was allowed to react at 60° C. for 60 min. The operations were basically the same as that in Example 10. The results showed that the conversion of p-fluoronitrobenzene was 100%, and the selectivity for p-fluoroaniline was 99.99%.

Based on the Examples and the results, the catalyst of the disclosure exhibits efficient catalytic activity of hydrogenation of nitrobenzene, chloronitrobenzene, methylnitrobenzene, bromonitrobenzene, fluoronitrobenzene, and the like.

The catalyst is efficient in selective hydrogenation of p-chloronitrobenzene to prepare p-chloroaniline, and the conversion and selectivity for the target product both exceed 99%, and the side reaction of dichlorination is reduced.

The catalyst contains a relatively small amount of platinum compared with known hydrogenation catalyst, so it is cheap.

The reaction condition of the catalyst is mild, and the catalyst is easy to separate from the reaction solution.

$ZrO_2$ is dispersed on the mesoporous silica sieve SBA-15 to form a composite support and the platinum is carried by the composite support. The platinum and the $ZrO_2$ cooperate to produce concerted catalysis.

The catalytic reaction is triggered under UV irradiation, and no inert gas and no extra reducing agent are involved. The platinum is in the form of nanoparticles dispersed on the composite support $ZrO_2$/SBA-15, improving the catalytic performance.

It will be obvious to those skilled in the art that changes and modifications may be made, and therefore, the aim in the appended claims is to cover all such changes and modifications.

What is claimed is:

1. A method for preparing p-chloroaniline, the method comprising mixing a composition of matter and p-chloronitrobenzene in the presence of hydrogen, the composition of matter comprising platinum (Pt) and a composite support, the composite support comprising $ZrO_2$/mesoporous silica sieve SBA-15; wherein:
   platinum accounts for 0.01-0.3 wt. % of the composition of matter; and
   $ZrO_2$ accounts for 5-20 wt. % of the composite support.

2. The method of claim 1, wherein the platinum accounts for 0.05-0.15 wt. % of the composition of matter.

3. The method of claim 2, wherein the platinum accounts for 0.08-0.10 wt. % of the composition of matter.

4. The method of claim 1, comprising dissolving the composition of matter and p-chloronitrobenzene in absolute ethyl alcohol in a reactor, heating the reactor to a temperature of 40-90° C., and purging the reactor with hydrogen.

5. The method of claim 2, comprising dissolving the composition of matter and p-chloronitrobenzene in absolute ethyl alcohol in a reactor, heating the reactor to a temperature of 40-90° C., and purging the reactor with hydrogen.

6. The method of claim 3, comprising dissolving the composition of matter and p-chloronitrobenzene in absolute ethyl alcohol in a reactor, heating the reactor to a temperature of 40-90° C., and purging the reactor with hydrogen.

7. The method of claim 4, wherein the reactor is heated to a temperature of 50-70° C.

8. The method of claim 5, wherein the reactor is heated to a temperature of 50-70° C.

9. The method of claim 6, wherein the reactor is heated to a temperature of 50-70° C.

* * * * *